United States Patent [19]

Vogt et al.

[11] Patent Number: 5,619,804
[45] Date of Patent: *Apr. 15, 1997

[54] ANATOMICAL MEASURING TAPE WITH INDICATOR

[76] Inventors: Katie S. Vogt, 275 Engle St., Apt. B-2, Englewood, N.J. 07631; David Porat, 18 Sunset Rd., Newton, Mass. 02158

[*] Notice: The term of this patent shall not extend beyond the expiration date of Pat. No. 5,414,943.

[21] Appl. No.: 446,944

[22] Filed: May 15, 1995

Related U.S. Application Data

[63] Continuation-in-part of Ser. No. 150,812, Nov. 12, 1993, Pat. No. 5,414,943.

[51] Int. Cl.⁶ ..................................................... G01B 3/10
[52] U.S. Cl. ................... 33/763; 33/764; 33/765; 33/759; 33/512
[58] Field of Search ............................. 33/758, 762, 763, 33/764, 759, 2 R, 512

[56] References Cited

U.S. PATENT DOCUMENTS

| | | |
|---|---|---|
| 208,346 | 9/1878 | Taylor . |
| 870,884 | 11/1907 | Hollinger . |
| 940,256 | 11/1909 | Kennedy et al. . |
| 1,216,418 | 2/1917 | Crogan . |
| 2,205,626 | 6/1940 | Mason . |
| 2,230,668 | 2/1941 | Ohrtmann . |
| 2,240,753 | 5/1941 | Bouchard et al. . |
| 2,271,725 | 2/1942 | Tunnicliff . |
| 2,559,501 | 7/1951 | Graf . |
| 2,946,125 | 7/1960 | Gittelson . |
| 3,426,435 | 2/1969 | Ballard et al. . |
| 3,885,314 | 5/1975 | Banas, Sr. . |
| 4,164,816 | 8/1979 | Bergkvist ........................ 33/764 |
| 4,178,691 | 12/1979 | Tateishi ........................... 33/762 |
| 4,195,348 | 3/1980 | Kakutani ......................... 33/763 |
| 4,506,446 | 3/1985 | Mitchell . |
| 5,027,526 | 7/1991 | Crane ............................. 33/763 |
| 5,414,943 | 5/1995 | Vogt ............................... 33/764 |

FOREIGN PATENT DOCUMENTS

| | | | |
|---|---|---|---|
| 619269 | 9/1935 | Germany . | |
| 235009 | 11/1985 | Japan ............................. | 33/763 |
| 116021 | 3/1946 | Sweden ......................... | 33/762 |
| 361776 | 6/1962 | Switzerland . | |
| 885976 | 1/1962 | United Kingdom ........... | 33/2 R |
| 2217459 | 10/1989 | United Kingdom ........... | 33/763 |

OTHER PUBLICATIONS

Advertising brochure entitled "Model CTB Constant Torque Hinge", Reell Precision Manufacturing Corporation, 1259 Wolters Blvd., St. Paul, Minnesota 55110, U.S.A.

Primary Examiner—Thomas B. Will
Attorney, Agent, or Firm—Gottlieb, Rackman & Reisman, P.C.

[57] ABSTRACT

A measuring device having, in one embodiment, two measuring tapes held on separate reels in a housing. The housing has two windows for displaying measurement indicia appearing on each tape. Alternatively, electronic digital displays are used to show the measurements. The tapes are spring biased toward the fully wound condition. Each tape has a button controlled clutch locking each respective tape in an extended condition. In a preferred application, a user draws a first tape around her torso just below the breasts, connects the tape to the end of the second tape at the housing, and locks this tape when taut. The device is moved upwardly, now encircling the breasts also, and the second tape is extended to accommodate the additional girth. The second clutch locks the second tape in position. The device is removed from the user's body, and sizes displayed in the windows are read. The first tape measures and indicates rib cage girth, and the second tape converts the additional measurement to cup sizes. The windows expose only the relevant data from each respective tape, maintaining the data visible while the tapes are locked in the extended condition. When the clutches are released, both reels rewind. In another embodiment a single tape is used for determine both measurements and electronic circuitry is used to translate the measurements into nominal sizes.

16 Claims, 9 Drawing Sheets

ANATOMICAL MEASURING TAPE WITH INDICATOR

RELATED APPLICATIONS

This is a continuation-in-part to application Ser. No. 150,812, filed Nov. 12, 1993, now U.S. Pat. No. 5,414,943.

BACKGROUND OF THE INVENTION

1. Field of the Invention

The present invention relates to a device for making plural anatomical measurements, and displaying the results. The purpose of the device is to identify an appropriate apparel size for a user.

More particularly, the specific embodiment chosen as an exposition of the details of the invention is a tape type device which provides a direct readout of the two measurements determining the size of a woman's brassiere.

2. Description of the Prior Art

Adaptation of a measuring tape, or the like, to determine appropriate apparel sizes has long been attempted, as will be seen from the prior art. The reader will note that most, if not all, apparel tapes require a second person to measure the first.

U.S. Pat. No. 2,559,501, issued to Fred V. Graf on Jul. 3, 1951, discloses a device which is essentially donned in the manner of a brassiere, there being graduated indicia provided on transparent cups for measuring breast size, in addition to indicia provided on the strap encircling the torso for determining bust girth. There is a buckle provided between cups to establish a satisfactory separation of the breasts. This device must be manipulated in at least six operational steps in order to yield results. The inventor teaches assistance by another person in employing the device. Contrast this with the instant invention wherein a self-operated device is provided which can be easily manipulated and which provides a direct readout of the final clothing size for which the tape has been designed.

U.S. Pat. No. 2,946,125, issued to Bernard Gittelson on Jul. 26, 1960, discloses a harness comprising five graduated straps. Gittelson produces indirect measurements, i.e., requiring calculation of measured data, as opposed to displaying a final, usable value or standard size.

A measuring tape having measurements on opposing sides is seen in U.S. Pat. No. 3,292,261, issued to Madeline L. Hayes on Dec. 20, 1966. The tape is held encircling the torso, and a benchmark indicates an appropriate size. A separate tape member is then attached, so that markings indicative of cup size become visible. The tape is then again placed around the torso, this time encircling the breasts, and one marking indicative of cup size is brought into registry with the previously determined torso girth.

U.S. Pat. No. 3,849,886, issued to Nola D. Weyrick et al. on Nov. 26, 1974, discloses a tape measure adapted to include removable markers for recording measurements. When the tape encircles the body, one end meeting the tape at an intermediate point a marker is adhered at that point. The marker includes indicia identifying which measurement resulted in the indicated value.

U.S. Pat. No. 4,211,011, issued to Ilamae W. Jacobson on Jul. 8, 1980, discloses a body garment incorporating a plurality of body encircling measurement tapes. Each tape is adhered in its snug position, and indicates a measured circumference. After all tapes are adhered, they remain in place as a part of the garment to be worn.

U.S. Pat. No. 4,875,296, issued to John P. Holzmeister et al. on Oct. 24, 1989, discloses a device comprising a tape measure and a frictional retaining member. The tape is passed around the body of a user, and is passed through the retaining member. The device can be held in this position by pulling with one hand, the other hand remaining free to record the measurement. The measurement is determined in similar fashion to that employed in reading a standard tape measure; that is, aligning the zero dimension end with a measured value. The Holzmeister et al. invention enables holding the tape measure in its deployed position with but a single hand.

None of the above inventions and patents, taken either singly or in combination, is seen to describe the instant invention as claimed.

OBJECTIVES AND SUMMARY OF THE INVENTION

The present invention provides a tape measure which can be successfully used by one person to measure one's own body. It can therefore be used by women who wish to determine apparel size, by themselves, and not be reliant upon an assistant.

In one embodiment of the invention, a housing encloses two reels, each paying out a measuring tape. A first tape is extended around the body, and locked in the extended condition, once its free end has encircled the torso and met the housing. The reels are spring biased to rewind, so that the device is retained in its position encircling the body by resilient grip. This frees the user's hands to manipulate the device, repositioning the same about the bust.

Since the first tape is locked to extend from the housing the distance equivalent to the girth, the second tape is now paid out to accommodate the additional girth. The second tape can also be locked. Each tape displays the paid out dimension through windows formed in the housing, and these values are maintained if the tapes are locked in position. The device can be removed from the body, and the values displayed can be clearly read.

The novel measuring device is readily operated by one person, and the values obtained thereby are easily read once the device is removed from the body. The tapes are quickly rewound by releasing the two locks.

The device is self-supporting in place on the body, in both positions, so that the user can remove her hands therefrom, and reposition the hands for subsequent handling thereof.

The instant invention avoids certain situations encountered in the prior art, such as requiring further calculations or conversions to arrive at final, usable values, preferably in the form of recognized standard sizes. Instead, the device reads out final apparel sizes. This is accomplished by incorporating a well known formula in the intimate apparel industry as will be hereinafter described. The first tape measures the rib cage ($R_1$) under the bust and is calibrated such that the readout is the actual measurement plus 5, i.e., $R_1+5$, to correspond to the band size on a brassiere. The second tape is calibrated to incorporate the formula wherein the cup size corresponds to the bust size measurement ($R_2$) minus the rib cage measurement plus five ($R_2-(R_1+5)$).

In an alternate embodiment of the invention, electronic means are provided to measure the lengths of tapes being paid out from the housing. An electronic display is also provided for showing the measurements thus obtained. In a further alternate embodiment a single tape is used to obtain both measurements.

3

Accordingly, it is a principal objective of the invention to provide an anatomical measuring device which is readily operable by one person in full and complete privacy.

It is another objective of the invention to provide an anatomical measuring device which makes all calculations, and displays final, usable values.

It is another objective of the invention to provide an anatomical measuring device in which the displayed final useable values are permanently and fixedly displayed until deliberately removed in preparation for another measurement.

It is a further objective of the invention to provide an anatomical measuring device which is self-supporting on the body of the user.

it is an additional objective of the invention to provide an anatomical measuring device which is uncomplicated, and which employs well known apparatus, such as tape measures, whereby it is quickly mastered by a user.

Another objective of the invention is to provide an anatomical measuring device which maintains the displayed values until released by the user.

It is a further objective of the invention to provide an anatomical measuring device which stores its measuring tapes within a compact housing, and biases the tapes into the stored condition.

It is a general goal of the invention to provide improved elements and arrangements thereof in an apparatus for the purposes described which is inexpensive, dependable and fully effective in accomplishing its intended purposes.

It is submitted that the present invention meets or exceeds all the above objects and goals. Upon further study of the specification and appended claims, further objects and advantages of this invention will become apparent to those skilled in the art.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

4

Figure 8:
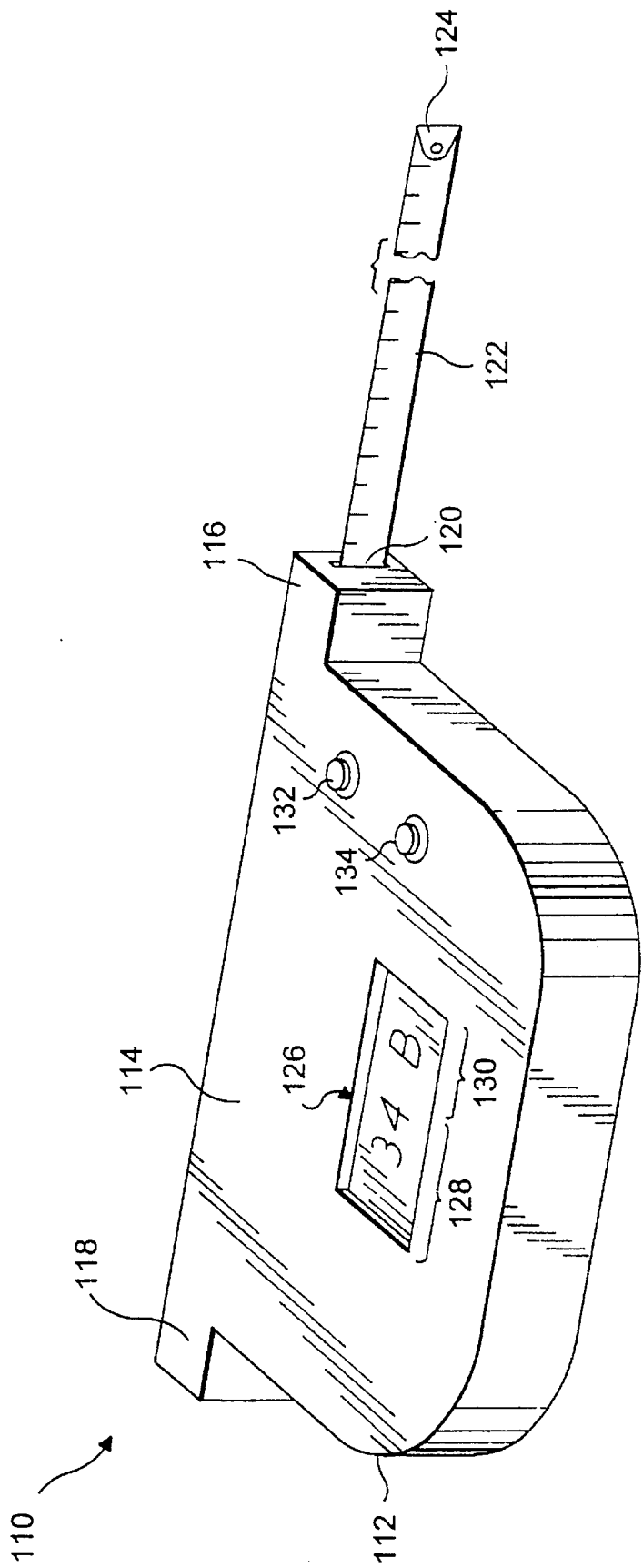
FIG. 8 shows a perspective front elevational view of a first alternate embodiment of the invention.
Figure 9:
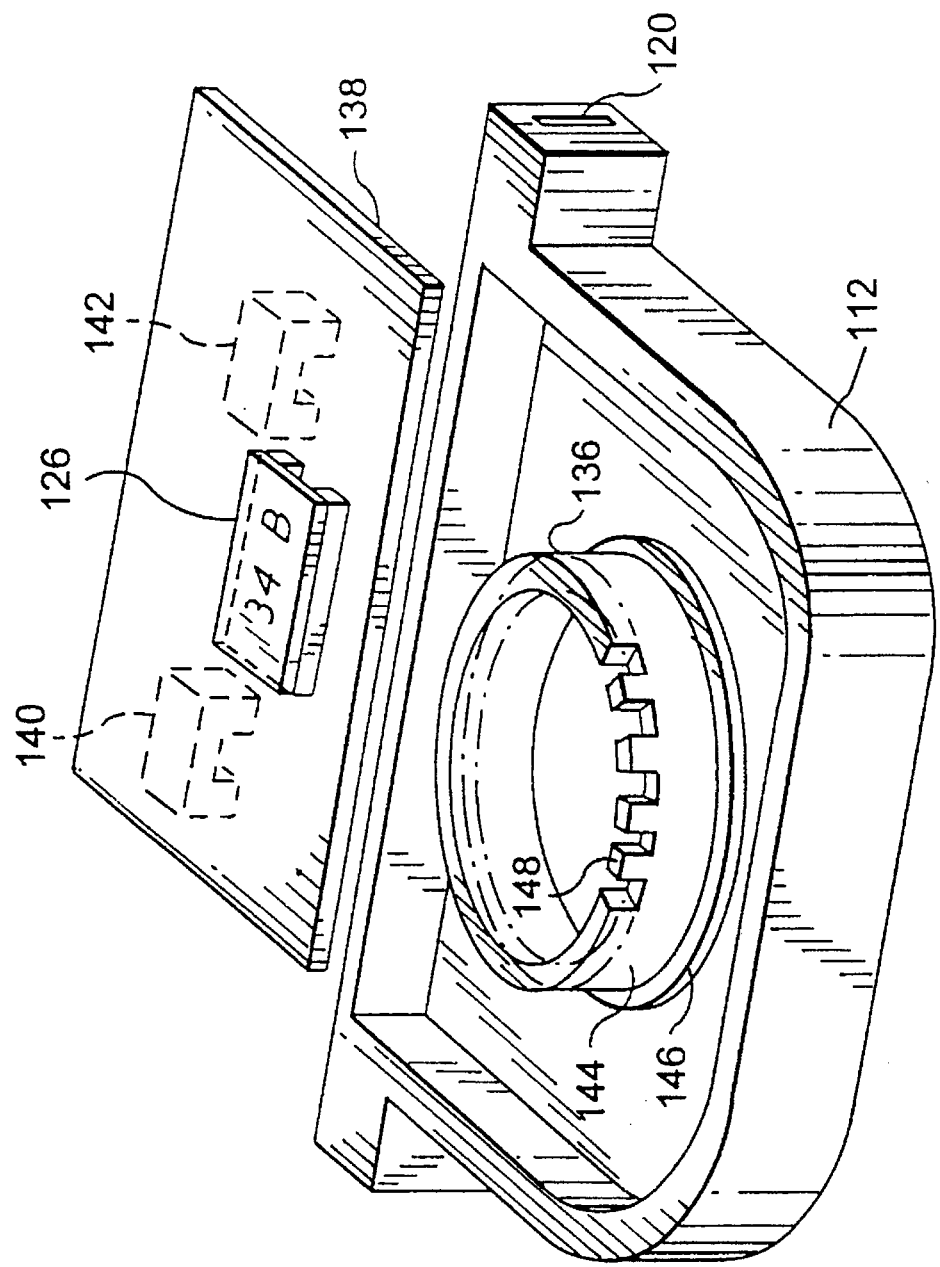
Figure 10:
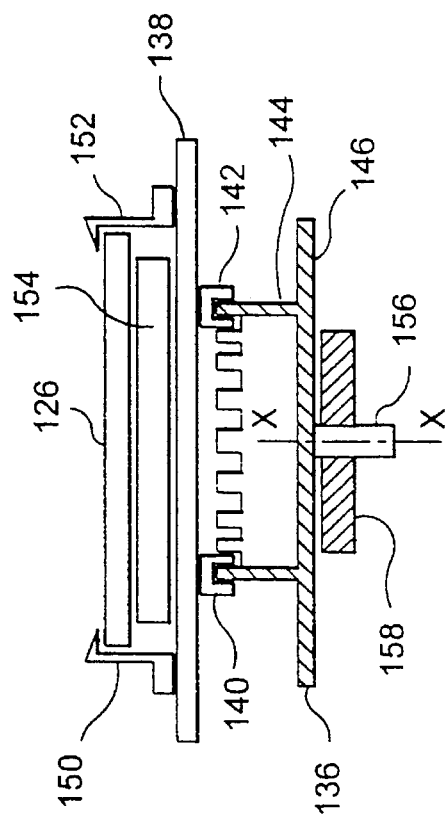
Figure 11:
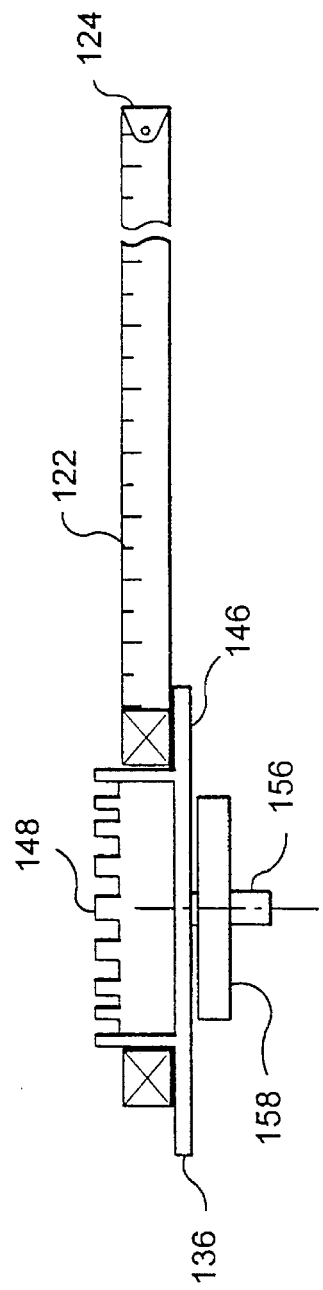
Figure 12:
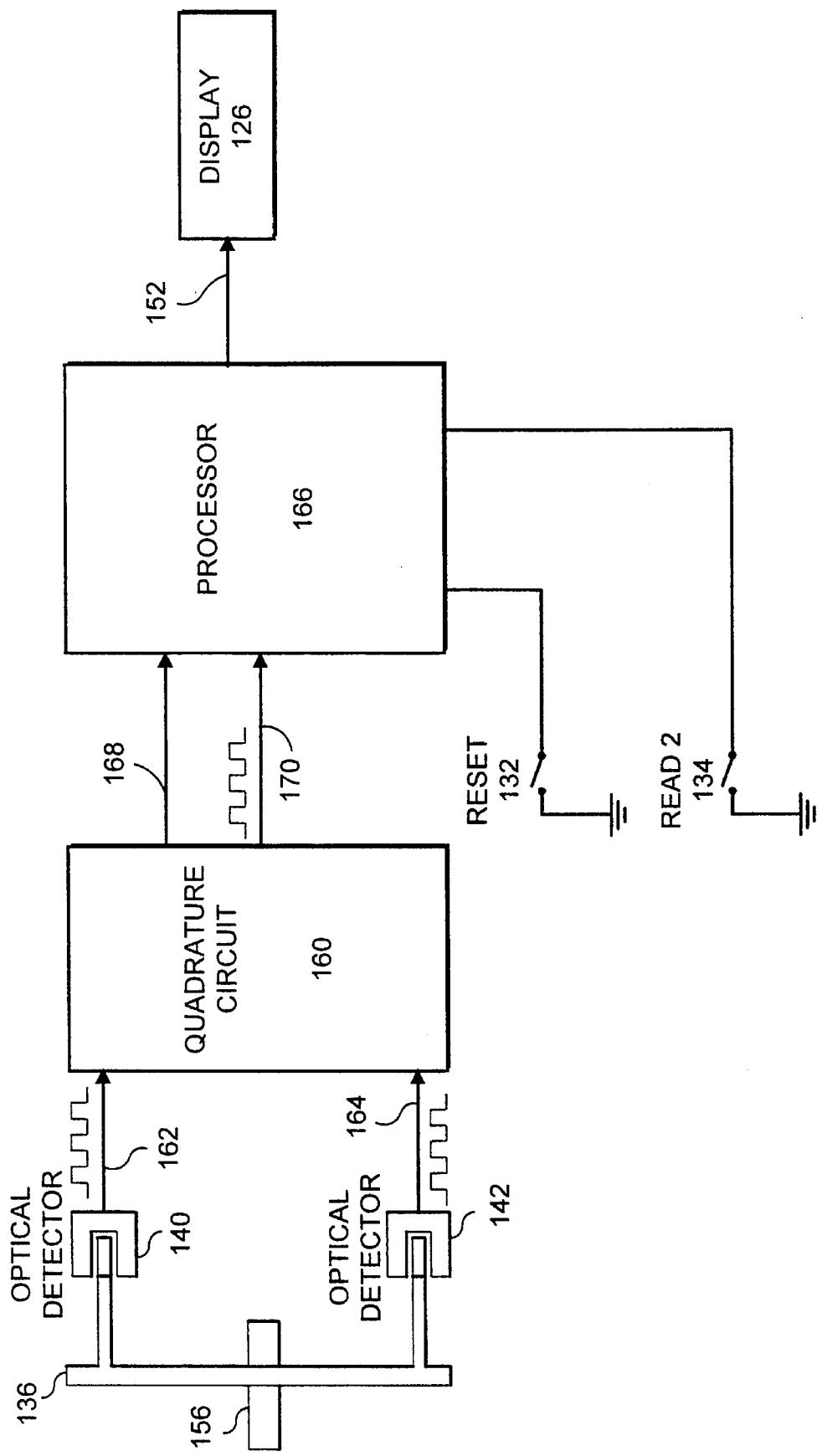
Figure 13:
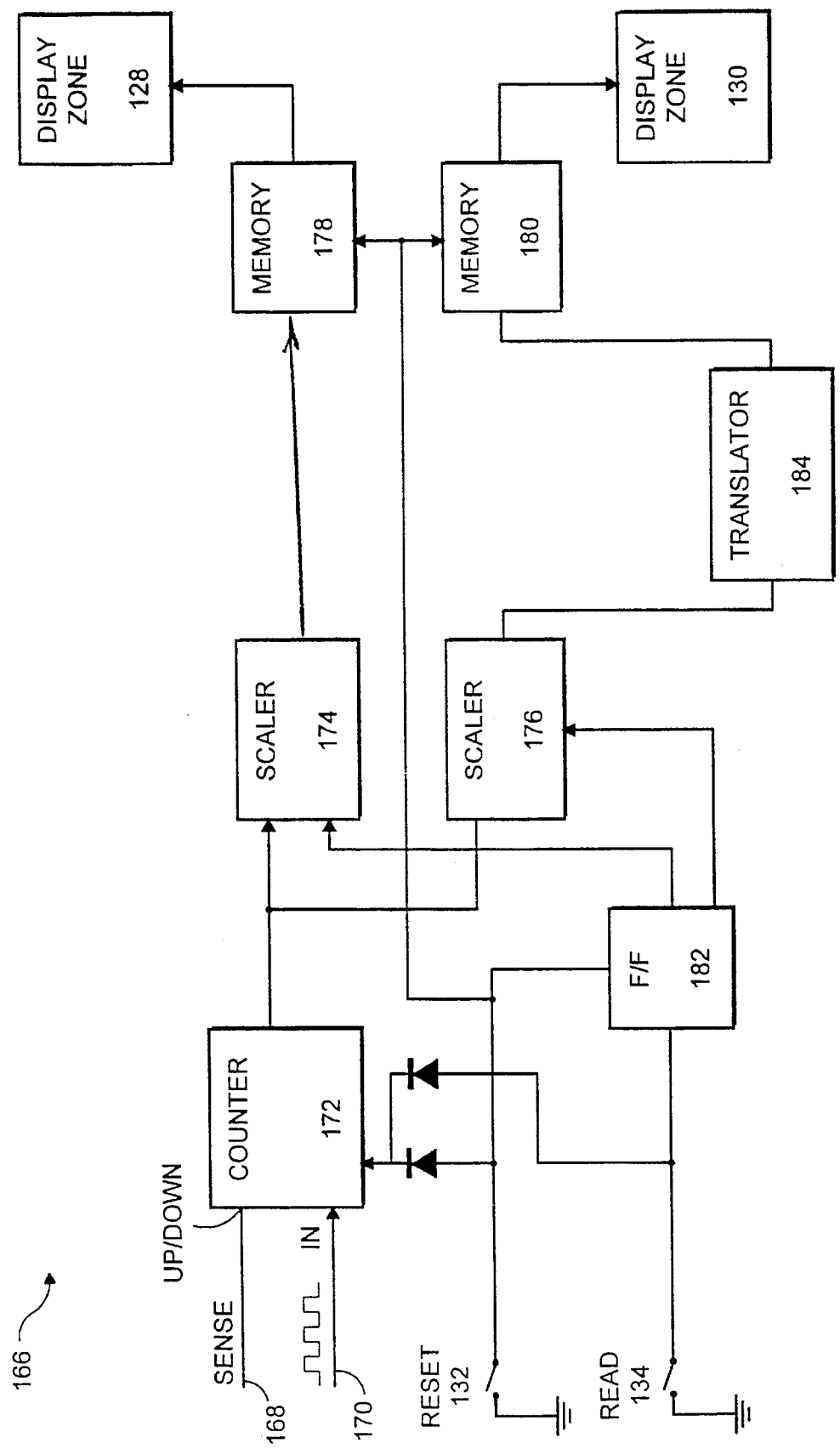

FIG. 9 shows details of the embodiment of FIG. 8;

FIG. 10 shows a side-sectional view of the chopper wheel assembly for the embodiment of FIG. 8;

FIG. 11 shows the tape being paid off the chopper wheel;

FIG. 12 shows a block diagram of the electronic circuitry for the embodiment of FIG. 8;

FIG. 13 shows details of the processor of FIG. 12; and

Figure 14:
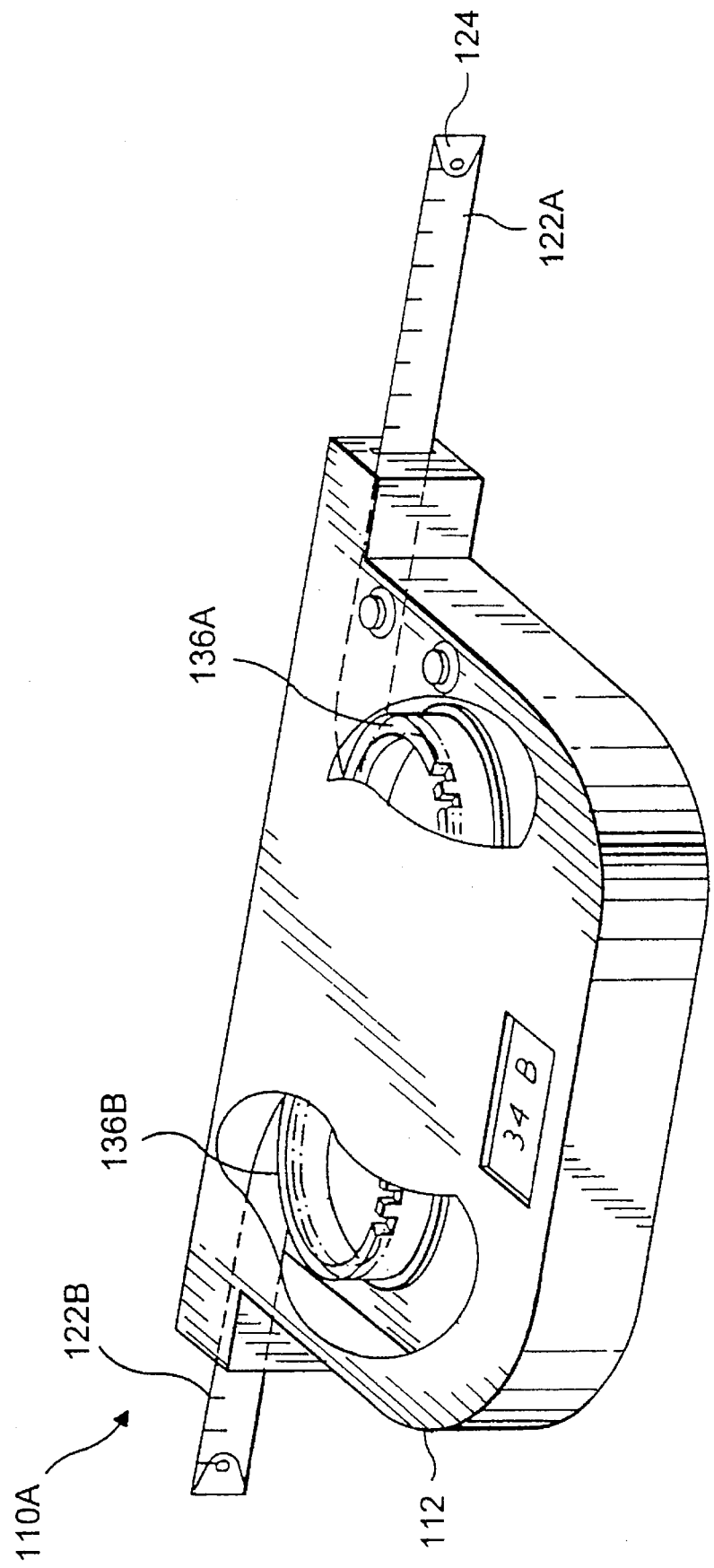

FIG. 14 shows a cross-sectional view of a second alternate embodiment of the invention.

DETAILED DESCRIPTION OF THE INVENTION

Figure 1:
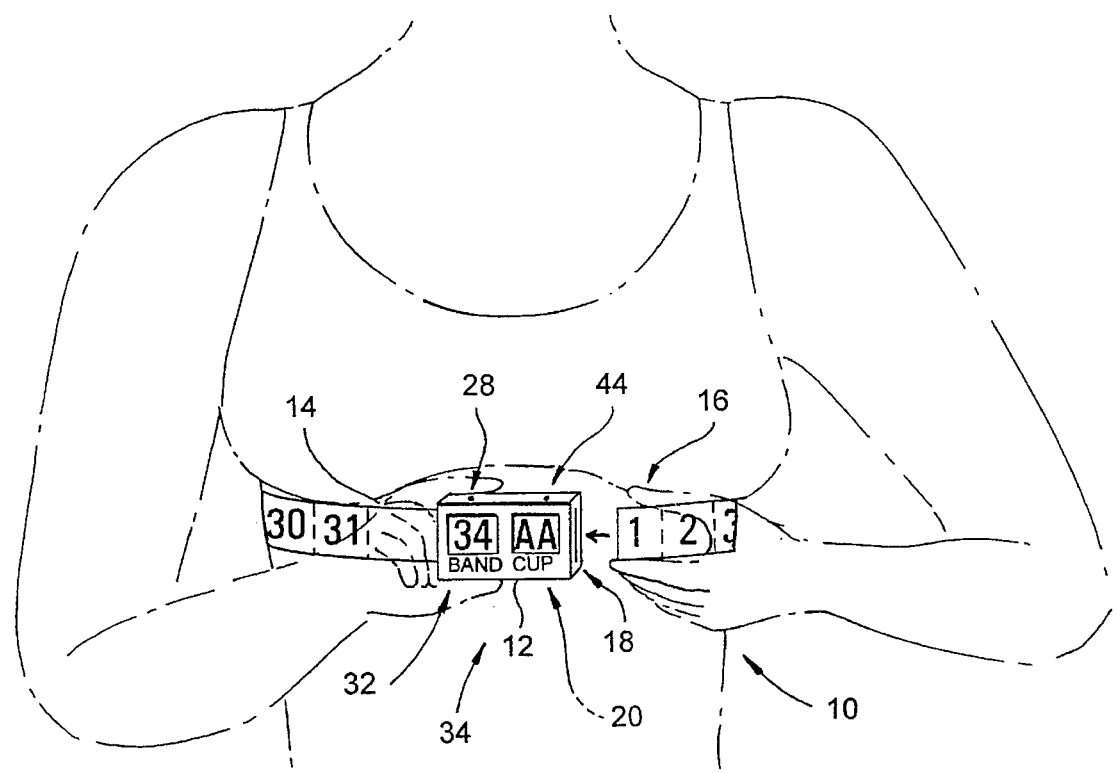
FIG. 1 is an environmental, front elevational view of a first embodiment of the invention, showing a first measurement step.
Figure 4:
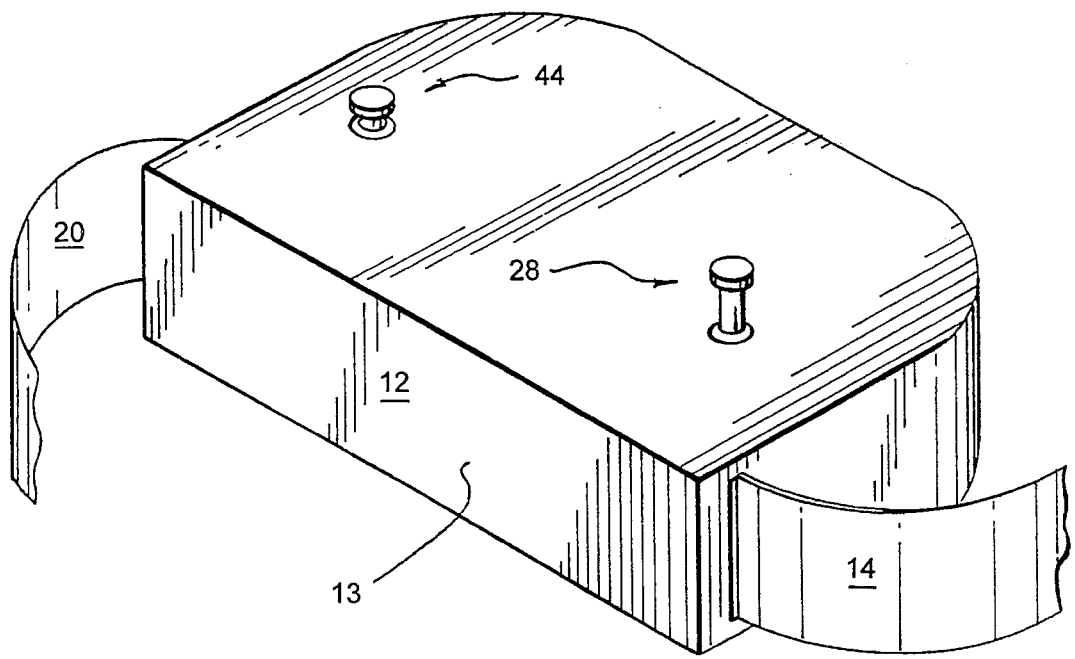
Figure 5:
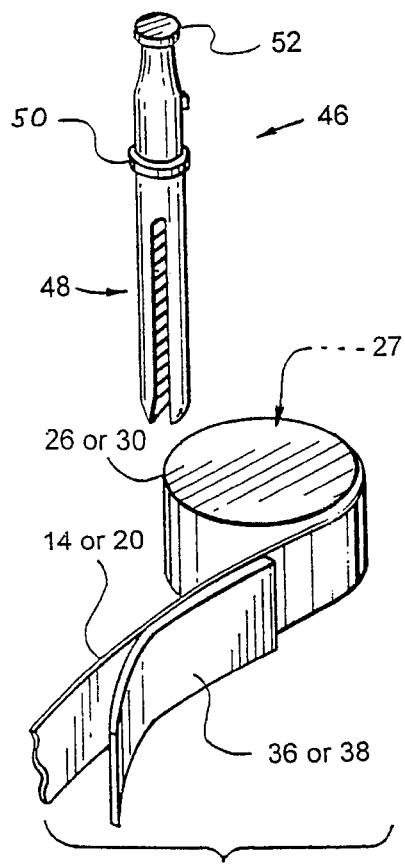
FIG. 5 is a perspective detail view of a locking mechanism, a partial measuring tape, and a guide member, for the embodiment of FIG. 1, and drawn to enlarged scale.
Figure 6:
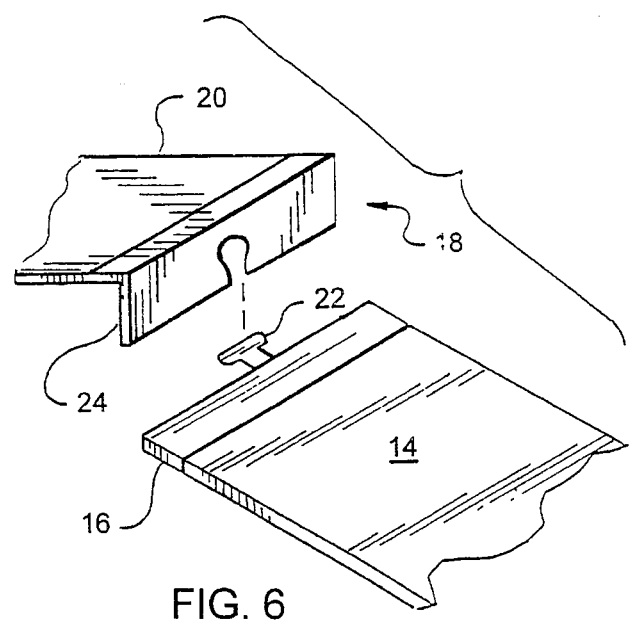
FIG. 6 is a perspective detail view of connection members for attaching the ends of the tapes together, drawn to enlarged scale, for the embodiment of FIG. 1.

Turning now to FIG. 1 of the drawings, the anatomical measuring device 10 is shown placed about the torso of a user so as to take the first of two measurements. A housing 12 containing two measuring tapes is held in one hand at any convenient point below the breasts, and a first measuring tape 14 is grasped in the other hand and paid out. Free end 16 is held in the second hand, passed around the back, and is returned to housing 12. Free end 16 can be latched to free end 18 of second measuring tape 20 by inter-engaging members 22, 24 (see FIG. 6) disposed at respective free ends 16, 18. At this point, device 10 is self-supporting, resiliently clinging to the torso under tension imposed by its respective reel 26 (see FIG. 7), which has a spring 27 (see FIG. 5) biasing reel 26 to rewind. As the device 10 is held under this tension, a flat wall 13 (best shown in FIG. 4) of the housing 12 is held substantially in full contact with the user's body, to guarantee the accuracy of the measurements obtained by the device 10.

Figure 2:
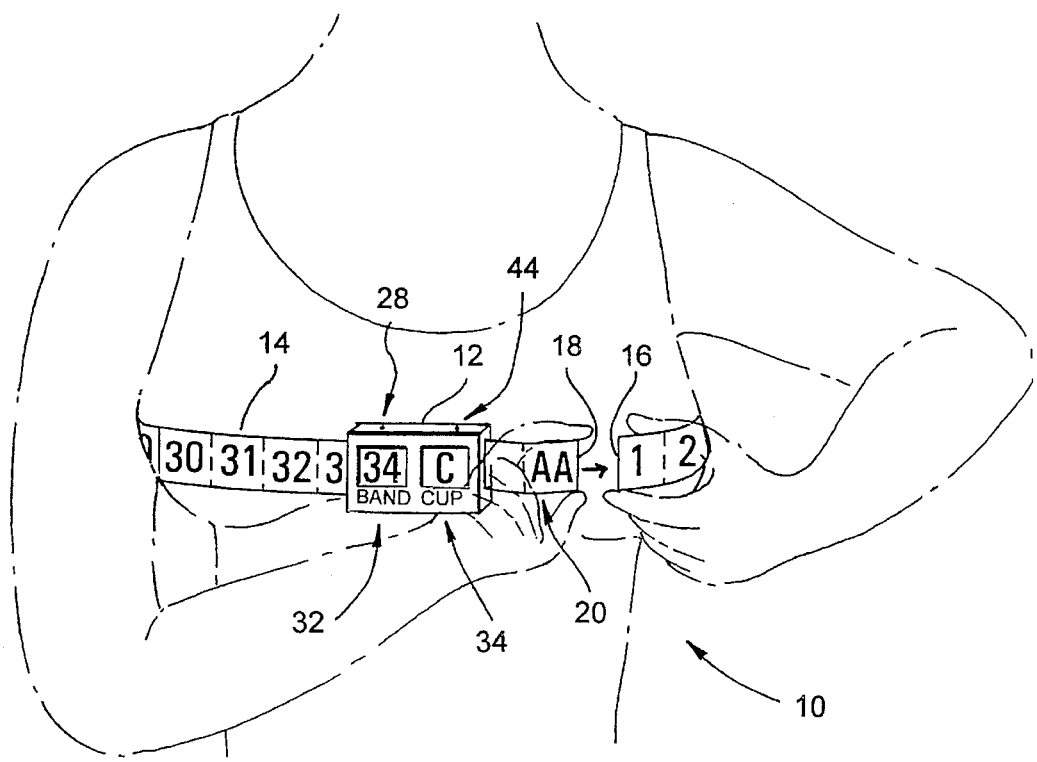
FIG. 2 is an environmental, front elevational view of the embodiment of FIG. 1, showing a second measurement step.

A first locking mechanism 28, which will be explained hereinafter, immobilizes first measuring tape 14. Free ends 16, 18 are unlatched, and device 10 is repositioned over the bust, as shown in FIG. 2. Second measuring tape 20 wound on reel 30 is paid out until its respective free end 18 meets free end 16 of first measuring tape 14. Reel 30 includes a second spring 31 also biasing its respective reel 30 to rewind.

Indicia are placed on first and second measuring tapes 14, 20, arranged to allow for the width of housing 12, and located so as to be visible in windows 32, 34 formed in housing 12. First measuring tape 14 bears indicia corresponding to inch, or metric values, if desired, increments within a generally accepted range encompassing those chest sizes recognized by the apparel industry. Second measuring tape 20 bears indicia in the form of letters, arranged to correspond to brassiere cup sizes recognized by the apparel industry. Low or small values appear on free ends 16 and 18, so that the maximum measured value is framed in window 32 or 34 when a respective measuring tape 14 or 20 is extended.

Reels 26 and 30 are disposed adjacent one another, and hence the wound portions of measuring tapes 14 and 20 are adjacent. An alphanumeric value is thus collectively displayed in windows 32 and 34 when the second measurement is taken. In the presently contemplated preferred embodiment, it is envisioned that these readouts would encompass the ranges of thirty two through fifty two inches in the case of measuring tape 14 and between cup measurements A through DDD in the case of measuring tape 20. This value can be remembered or recorded., and no further calculation or conversion is required.

Figure 7:
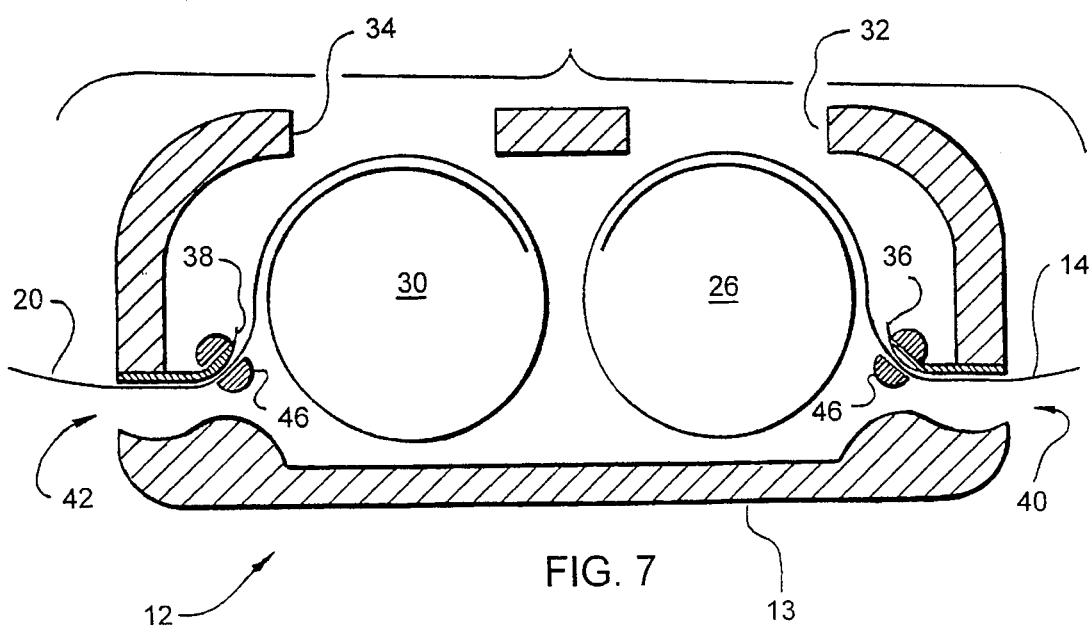
FIG. 7 is a diagrammatic, cross sectional, top plan view of the housing and its principal components, drawn to enlarged scale, for the embodiment of FIG. 1.

With reference to FIG. 7, housing 12 is seen to enclose reels 26 and 30. A portion of each measuring tape 14 or 20 passes beside a thin metal guide 36 or 38, and passes through a slot 40 or 42 to the exterior of housing 12.

Locking mechanisms 28, 44 will now be explained, both being substantially identical, but mirror image to one another. A bore (not shown) formed in housing 12 accepts a generally cylindrical locking member 46, better seen in FIG. 5, having a clevis 48 which straddles both measuring tape 14 or 20 and respective guide 36 or 38. When pushed downwardly, locking member 46 resiliently pinches measuring tape 14 or 20 to guide 36 or 38, thus immobilizing measuring tape 14 or 20. When locking member 46 is pulled upwardly, grip on measuring tape 14 or 20 is relaxed, and respective reel 26 or 30 rewinds measuring tape 14 or 20 if 2 not restrained by being held by hand.

A shoulder 50 formed in locking member 46 abuts a corresponding shoulder (not shown) in housing 12, thereby limiting vertical travel, and preventing removal of locking member 46 from housing 12.

Figure 3:
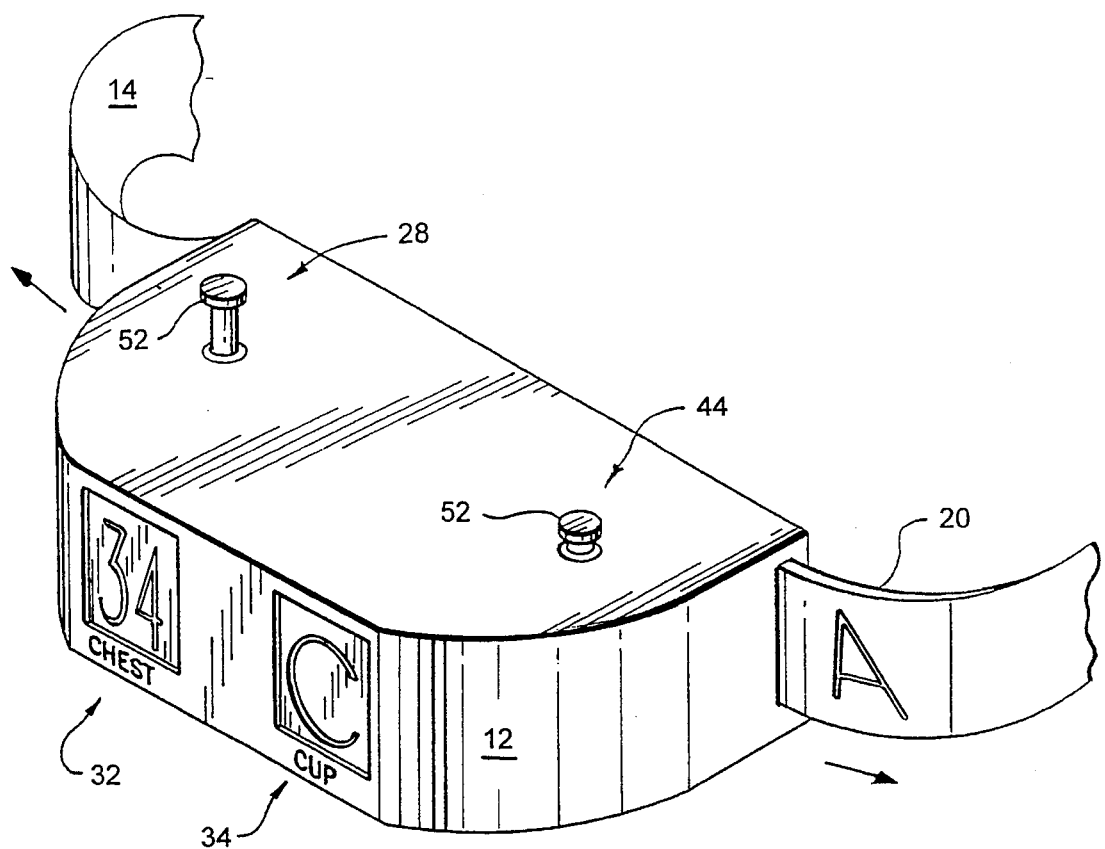
FIGS. 3 and 4 are, respectively, front and rear perspective views of the housing of the embodiment of FIG. 1 with measuring tapes broken away, and drawn to enlarged scale.

As seen in FIG. 3, there are two locking mechanisms 28, 44. One locking mechanism 44 is shown pushed down in the locked position at the right of this view, and the other locking mechanism 28 is shown pulled up, in the released position. Each locking mechanism 28 or 44 has a head 52 enabling grasping by a user, so that it may be readily pulled into the released position.

FIGS. 8–14 show other embodiments of the invention. In these embodiments, the same general principles are used as in the embodiment described above, however, instead a mechanical arrangement and display, electronic means are used. Moreover, preferably a single measurement tape is used thereby reducing the complexity of the apparatus and its operation significantly.

In the embodiment of FIG. 8, the measurement apparatus 110 consists of a housing 112 having a top surface 114 and two opposed lateral extensions 116, 118. The lateral extension 116 includes a slot 120 through which a measuring tape 122 is paid out. Tape 122 has a free end 124. Lateral extension 118 has a latch (not shown) for securing the free end 124 after the tape has been paid out, as discussed more fully below.

Top surface 114 includes an electronic display 126 with a first display zone 128 and a second display zone 130. In addition, mounted on the top surface 114 are two momentary push-button switches 132 and 134. Optionally, a power switch (not shown) may be provided on the housing for selectively turning the apparatus 110 on and off.

Referring now to FIGS. 9 and 10, inside housing 112 there is provided a chopper wheel 136, and a printed circuit board 138. The display 126 is above the board 138. Two optical sensors 140, 142 are mounted on the bottom of the board 138, together with other electronic elements shown in FIG. 12 and discussed below.

Chopper wheel 136 is generally cylindrical in shape to define a tubular tape bearing reel 144. At the lower end, the reel 144 is terminated with an annular rim 146. The tape 122 (not shown in FIGS. 9 and 10 for the sake of clarity) is wound on the reel 144 so that it rests on the rim 146, as seen in FIG. 11. Above tape bearing reel 144, the wheel 136 is provided with a plurality of axially oriented teeth 148 extending circumferentially about the wheel 136.

As best seen in FIG. 10, the apparatus 110 is assembled so that the wheel 136 is rotatable about an axis X—X normal to printed circuit board 138. The wheel and the board are positioned so that the teeth 148 pass between the gaps of the optical sensors 140, 142. The display 126 is maintained above the board 138 by a pair of brackets 150, 152 with a connector 154 providing the driving signals from the board 138 to the display 126.

Wheel 136 further includes an axle 156 which rotatably mounts it on housing 112. An escapement mechanism 158 may be provided optionally on the axle 156 to selectively lock the wheel 136 in place if required as described for the embodiment of FIGS. 1–7.

The wheel 136 is spring loaded just like reels 26, 30 in FIG. 7 to allow the tape 122 to be paid out or withdrawn from the housing 112 at will. However, if the tape end 124 is latched to the lateral section 118, it is automatically tensioned so that it is disposed smoothly and evenly about the body of the person. The length of tape 122 withdrawn from the housing 110 is measured and displayed as discussed below. After the measurement is completed, the tape is released and it automatically withdraws into the housing 110.

Referring now to FIGS. 12 and 13, the two optical sensors 140, 142 are connected to a quadrature sensor circuit 160. As the wheel 136 rotates in one direction or the other, due to the movement of tape 122, the teeth 148 pass through the appropriate gaps in the optical sensors 140, 142, and in response, the two sensors generate two respective pulse trains to the quadrature circuit 160 on lines 162, 164 respectively. Importantly the two pulse trains are preferably out of phase by a preset angle, such as 90°. This may be accomplished by either offsetting the two optical sensors so that they do not lie diametrically opposite each other across the wheel 136, or alternatively, by providing an odd number of teeth 148 on wheel 136. By comparing these two trains, the quadrature circuit makes a determination as to whether the wheel is turning in one direction, for example to pay off tape 122, or the other, i.e., retracting tape. 122. This information is provided by circuit 160 to a processor 166 on line 168. In addition, the quadrature circuit 160 also generates a train pulse to the processor 166 on line 170. This latter train pulse may be identical to the train pulse from either sensor 140 or 142. The processor is also connected to switch 132, a reset switch, as well as switch 134, a count control switch. The processor generates outputs on connector 152 to display 126 using the signals received from the quadrature circuit 160 and switches 132 and 134.

More particularly, as shown in FIG. 13, the processor 166 includes an up/down counter 172 which receives the signals on lines 168 and 170. The signal on line 168 is coupled to the up/down control gate of the counter 172. The output of the counter 172 is provided to two scalers 174, 176. The outputs of the scalers are fed to two respective latching memories 178, 180. The scalers 174, 176 multiply the output of the counter by a preselected scaling factor, and also provide a linear offset, as described below.

Either one or another of scalers 174, 176 is used to scale the output of the counter 172, depending on the state of a flip/flop 182. The flip/flop 182 is controlled by READ switch 134. The elements shown in FIG. 13 are incorporated in the processor 166 either as discrete elements or, preferably as software routines.

The apparatus of FIGS. 8–13 operates as follows. Initially a woman pushes the RESET switch 132. This causes the counter 172, flip/flop 182 and memories 178, 180 to be reset. Then she withdraws the tape 122 from the housing 110, wraps it around her rib cage (in a manner similar to FIG. 1.), secures the end 124 of the tape to the section 118 and releases the tape 122. While this step is taking place the counter generates a count proportional to the length of tape 122 withdrawn from the housing 110. This count is fed to the scaler 174 which scales the count and adds to it an offset, for example, of 5 inches. For example, for every number $N_1$ scaler 174 generates a number $S_1$ where $S_1=N_1*k_1+5$. The constant $k_1$ is the proportionality constant converting the number of teeth 138 into inches. The product $N_1*k_1$ is the parameter $R_1$ discussed above. This formula is a standard formula known in the industry for converting the rib cage size to the brassiere band size. The size $S_1$ may be rounded to an even number, if so desired, as is standard practice in the industry.

The number $S_1$ is stored in memory 178 and then displayed as the band size by display zone 128.

After the band size is obtained, the woman, or an assistant, pushes the READ button 134, indicating that now the cup size is to be measured. This resets the counter 172 and sets the flip/flop 182. The woman now releases the tape end 124 from the housing 110, repositions the tape 122 to pass over the bust, and then reattaches its end 124 to the housing as shown generally in FIG. 2. However, in contrast to the previous embodiment, now only the single tape 122 need to be manipulated. During this step, the output of counter 172, which is proportional to the difference between the measurements around the bust and the rib cage, is now scaled by scaler 176. More particularly every count $N_2$ from the counter 172 is now multiplied by a second constant $k_2$ to convert the number of teeth 148 into a product $P=K_2 \times N_2$ which is equivalent in inches to the difference between the parameters $R_2$ and $R_1$. This product P is offset by a factor of for example 5, if P is in inches to yield a cup size $S_2$, where $S_2=P-5$. This number $S_2$ is translated by a translator 184 into a corresponding letter value (i.e. A, B, etc.) using a conversion well known in the industry and then stored in memory 180. The contents of memory 180 are displayed by display zone 130.

In this manner the measurements are obtained using a single tape in an easy, accurate and fast operation. After the second measurement is obtained, the apparatus can be turned off or reset using switch 130 and used again for another measurement.

Another alternate embodiment is shown in FIG. 14. In this Figure apparatus 110A includes a housing 112 with two wheels 136A, 136B paying off two respective tapes 122A, 122B as shown. Each wheel is equipped with its own set of optical decoders, quadrature circuit and counter. The parameters $S_1$, $S_2$ described above are derived separately. The operation of this embodiment is similar to the one shown in FIGS. 1–7.

Thus it will be seen that an uncomplicated yet effective measuring device is disclosed which is easily grasped and operated, which displays measurement values in final format, and is readily operated by a person taking her own measurements.

It is to be understood that the present invention is not limited to the embodiment described above, but encompasses any and all embodiments within the scope of the following claims.

We claim:

1. An anatomical measuring device for measuring brassiere sizes, said brassiere sizes including a band size and a cup size, said measuring device comprising:

a housing;

a first measuring tape with first tape indicia thereon indicative of said band size, and having a first reel, said first measuring tape being unwindable from said first reel to an extended position; and a first tape free end;

a second measuring tape with second tape indicia thereon indicative of said cup size, and having: a second reel, said second measuring tape being unwindable from said second reel to an extended position; and a second tape free end;

said first and second measuring tapes and said first and second reels being disposed within said housing;

window means formed in said housing such that said indicia are visible through said window means;

first locking means for independently locking said first tape end to said housing in said extended position, said first tape being constructed and arranged to provide said band size when said first tape extends around a person's rib cage; and engaging means for connecting said first and second tape free ends together to provide said cup size when said tapes extend around a person's bust line.

2. The anatomical measuring device according to claim 1, wherein said first and second reels further include spring biasing means, said biasing means urging said first and second reels to rewind.

3. The anatomical measuring device according to claim 1, wherein said first locking means is manually adjustable between a locked and an unlocked position.

4. The anatomical measuring device according to claim 1, further including a second locking means for locking said second measuring tape in said extended position.

5. An anatomical device for determining the brassiere size for a user, said brassiere size being defined by a band size and a cup size, said device comprising:

a housing having first lateral dimension and a second longitudinal dimension substantially perpendicular to said first dimension;

reel means rotatably disposed in said housing;

measuring tape means disposed on said reel means and having at least one free end, said tape means being arranged and constructed to be paid off to a first and a second length, said first length being defined by said tape means being deployed from said housing in a substantially longitudinal direction about the user's rib cage; said second length being defined by said tape means being deployed from said housing in a substantially longitudinal direction about said person's bust, wherein said tape means is deployed from a substantially common lateral location along said housing for defining either said first or second lengths;

conversion means for converting said first length and second length to a specific band and cup size, respectively; and display means for displaying said band and cup size.

6. The device of claim 5 wherein said reel means includes a first reel and a second reel, and said tape means includes a first tape and a second tape wound about said first and second reels, respectively.

7. The device of claim 6 wherein said first length is defined by said first tape extending from said housing, about said rib cage and back to said housing; and wherein said second length is defined by said second tape extending by a third length from said housing, said second length being equal to the sum of said first and said third length.

8. The device of claim 6 wherein said conversion means includes first indicia on said first tape and second indicia on said second tape.

9. The device of claim 8 wherein said housing includes a display window for showing said first and second indicia.

10. The device of claim 5 wherein said reel means includes a single reel and said tape means includes a single tape disposed on said reel.

11. The device of claim 10 wherein said conversion means includes a first converter for converting said first length to said band size when said tape extends to said first length; and a second converter for converting said second length to said cup size as said tape extends from said first to said second length.

12. The device of claim 11 further comprising selection mean for selecting said second converter.

13. An electronic device for measuring the brassiere size of a person, said brassiere size including a band size and a cup size, said device comprising:

a housing;

tape dispensing means disposed in said housing for dispensing a single tape from said housing to a first position wherein tape is disposed about said person's rib cage to define a first tape length, and to a second position wherein tape is disposed about said person's bust to define a second tape length;

electronic measuring means disposed in said housing for measuring said first and second tape length to obtain a first and a second measurement signals, respectively;

conversion means for converting said measurement signals into a specific band and cup size parameter; and display means for displaying said specific band and cup size parameters.

14. The device of claim 13 further comprising reel means disposed in said housing for holding said tape means, said electronic measuring means measuring said first and second lengths from the rotation of said reel means as tape is dispensed from said housing.

15. The device of claim 13 further including selection means for selecting when said tape is in said first and second position.

16. The device of claim 13 wherein said conversion mean converts said first length at a first rate and converts at least a portion of said second length at a second rate, in accordance with said selection means.

* * * * *